US008907280B1

(12) United States Patent
Larson et al.

(10) Patent No.: US 8,907,280 B1
(45) Date of Patent: Dec. 9, 2014

(54) FAST ELECTRON MICROSCOPY VIA COMPRESSIVE SENSING

(71) Applicant: Sandia Corporation, Albuquerque, NM (US)

(72) Inventors: Kurt W. Larson, Cedar Crest, NM (US); Hyrum S. Anderson, Albuquerque, NM (US); Jason W. Wheeler, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 127 days.

(21) Appl. No.: 13/622,943

(22) Filed: Sep. 19, 2012

(51) Int. Cl.
*H01J 37/26* (2006.01)
*G01N 23/225* (2006.01)

(52) U.S. Cl.
USPC .......................................... 250/310; 250/307

(58) Field of Classification Search
CPC . H01J 37/26; H01J 2237/22; H01J 2237/226; H01J 2237/25; H01J 2237/26; H01J 2237/28; G01N 23/225
USPC ................................................. 250/306–311
See application file for complete search history.

(56) References Cited

U.S. PATENT DOCUMENTS

| | | | | |
|---|---|---|---|---|
| 5,557,105 | A | * | 9/1996 | Honjo et al. ................... 250/310 |
| 6,005,247 | A | * | 12/1999 | Baum ............................ 250/310 |
| 6,977,375 | B2 | * | 12/2005 | Yin et al. ........................... 850/6 |
| 7,777,201 | B2 | | 8/2010 | Fragner et al. |
| 8,115,183 | B2 | | 2/2012 | Platzgummer |
| 8,199,244 | B2 | | 6/2012 | Baraniuk et al. |
| 2006/0239336 | A1 | | 10/2006 | Baraniuk et al. |
| 2012/0038786 | A1 | | 2/2012 | Kelly et al. |
| 2012/0175527 | A1 | | 7/2012 | De Boer et al. |

OTHER PUBLICATIONS http://en.wikipedia.org/wiki/Microelectromechanical_systems, printed on Mar. 21, 2014.*
Donoho, "Compressed Sensing", IEEE Transactions on Information Theory, vol. 52, No. 4, Apr. 2006, pp. 1289-1306.*
Tropp, et al., "Computational Methods for Sparse Solution of Linear Inverse Problems," Retrieved at <<http://authors.library.caltech.edu/18597/1/Tropp2010p10179Pleee.pdf>>, Proc. IEEE, vol. 98, No. 6, Jun. 2010, pp. 948-958.
Platzgummer, et al., "eMET—50keV Electron Mask Exposure Tool Development Based on Proven Multi-beam Projection Technology," SPIE Photomask Technology BACUS, 2010, pp. 1-12.
Yin, et al., "Practical Compressive Sensing with Toeplitz and Circulant Matrices," Retrieved at <<http://www.caam.rice.edu/~wy1/paperfiles/Rice_CAAM_TR10-01.PDF>>, In proceedings of Visual Communications and Image Processing (VCIP), 2010, pp. 1-10.

(Continued)

*Primary Examiner* — Jack Berman
(74) *Attorney, Agent, or Firm* — Michael A. Beckett

(57) ABSTRACT

Various technologies described herein pertain to compressive sensing electron microscopy. A compressive sensing electron microscope includes a multi-beam generator and a detector. The multi-beam generator emits a sequence of electron patterns over time. Each of the electron patterns can include a plurality of electron beams, where the plurality of electron beams is configured to impart a spatially varying electron density on a sample. Further, the spatially varying electron density varies between each of the electron patterns in the sequence. Moreover, the detector collects signals respectively corresponding to interactions between the sample and each of the electron patterns in the sequence.

19 Claims, 11 Drawing Sheets

(56) References Cited

OTHER PUBLICATIONS

Bauerdick, et al., "Addressable Field Emitter Array: A Tool for Designing Field Emitters and a Multibeam Electron Source," Journal of Vacuum Science & Technology B: Microelectronics and Nanometer Structures, vol. 22, No. 6, Nov. 2004, pp. 3539-3542.

Iqbal, et al., "An Electromagnetically Focused Electron Beam Line Source," Review of Scientific Instruments, vol. 74, No. 11, Nov. 2003, pp. 4616-4619.

Pickard, et al., "Distributed Axis Electron Beam Technology for Maskless Lithography and Defect Inspection," Journal of Vacuum Science & Technology B: Microelectronics and Nanometer Structures, vol. 21, No. 6, Nov. 2003, pp. 2834-2838.

Kapl, et al., "Characterization of CMOS Programmable Multi-beam Blanking Arrays as Used for Programmable Multi-beam Projection Lithography and Resistless Nanopatterning," Journal of Micromechanics and Microengineering, vol. 21, 2011, pp. 1-8.

Groves, et al., "Distributed, Multiple Variable Shaped Electron Beam col. For High Throughput Maskless Lithography," Journal of Vacuum Science & Technology B: Microelectronics and Nanometer Structures, vol. 16, No. 6, Nov. 1998, pp. 3168-3173.

"Simion Ion and Electron Optics Simulator," Retrieved at <<http://simion.com/>>, Retrieval Date: Aug. 30, 2012, pp. 1-9.

Xiao, et al., "Fast Algorithm for Total Variation Image Reconstruction from Random Projections," Retrieved at <<http://arxiv.org/pdf/1001.1774v1.pdf>>, Jan. 12, 2010, pp. 1-18.

Platzgummer, et al., "eMET POC: Realization of a Proof-of-Concept 50 keV Electron Multibeam Mask Exposure Tool," SPIE Photomask Technology Bacus, 2011, pp. 1-7.

Kampherbeek, et al., "High Throughput Maskless Lithography," Retrieved at <<http://www.sematech.org/meetings/archives/litho/8352/pres/D2_ML_P03_JanKampherbeek.pdf>>, Litho Forum, 2008, pp. 1-27.

Tanimoto, et al., "Secondary Electron Detection for Distributed Axis Electron Beam Systems," Microelectronic Engineering, vol. 85, 2008, pp. 1786-1791.

Pease, et al., "High-Speed Scanning Electron Microscopy using Distributed-axis Electron Optics," IEEE Microprocesses and Nanotechnology, 2007, pp. 414-415.

* cited by examiner

FAST ELECTRON MICROSCOPY VIA COMPRESSIVE SENSING

STATEMENT OF GOVERNMENTAL INTEREST

This invention was developed under contract DE-AC04-94AL85000 between Sandia Corporation and the U.S. Department of Energy. The U.S. Government has certain rights in this invention.

BACKGROUND

Electron microscopes are used in neuroscience, cell biology, microtechnologies, material science, and so forth to collect large quantities of data. Commonly, an amount of time required to collect imagery using an electron microscope can be a hindrance. For example, various efforts to image a mouse brain have conventionally taken several months of dedicated scanning electron microscope imaging time for every cubic millimeter of tissue. Moreover, it may be desirable to collect terapixels of imagery, with resolution of approximately 10 $nm^2$ per pixel, orders of magnitude more quickly than conventional scanning electron microscopes can achieve. Such capability can elucidate the inner workings of complex biological systems, to enable new inspection methods for microcircuit process controls, and the like.

Conventional scanning electron microscopes acquire an image pixel-by-pixel by raster scanning a small electron beam across a sample and recording a signal with a single detector. While many optical systems commonly use an array of photodetectors, electron microscopy approaches generally employ a single detector (or small number of detectors on the order of ten detectors) due to operation of such detector (e.g., collecting nearby electrons). Further, an amount of time to acquire an image is typically limited by Nyquist conditions and signal to noise ratios (SNRs). For instance, the Nyquist conditions can involve every pixel being visited by an electron beam, one at a time. Further, a length of time that the electron beam dwells on a given pixel can be proportional to a desired SNR.

Various conventional scanning electron microscope designs can support developing an image of an area of a sample by sequentially measuring brightness values (e.g., determined by secondary or back-scattered electron detectors) of each pixel of the image. Conventional scanning electron microscopes typically include an electron source that generates electrons (e.g., field emission electron source). Moreover, conventional scanning electron microscopes commonly include an acceleration component that drives electrons away from the electron source and send the electrons down a column of the scanning electron microscope. The electrons can proceed down the column and pass through various lenses, such as a condenser lens, which can shape the distribution of electrons to provide desired geometric properties, and an objective lens, which focuses the beam on the sample surface. The lenses of the scanning electron microscope can be electromagnetic lenses that alter electrical properties of the electrons. Moreover, differing designs of conventional scanning electron microscopes can include disparate electromagnetic lenses. Conventional scanning electron microscopes also commonly include an aperture and a scanning coil. The electrons can impinge upon the aperture to reduce a broad beam of electrons down to a single narrow beam. For instance, the narrow beam can have a diameter on the order of a few nanometers or less than a nanometer. The scanning coils can be a set of electromagnetic components that can direct the beam coming from the aperture to a specified location on a sample, thereby allowing one pixel to be measured at a time. The beam can interact with the sample and a response can be measured at a detector. The foregoing can be repeated for each pixel to be scanned when generating the image of the sample.

SUMMARY

Described herein are various technologies that pertain to compressive sensing electron microscopy. A compressive sensing electron microscope includes a multi-beam generator and a detector. The multi-beam generator emits a sequence of electron patterns over time. Each of the electron patterns can include a plurality of electron beams, where the plurality of electron beams is configured to impart a spatially varying electron density on a sample. Further, the spatially varying electron density varies between each of the electron patterns in the sequence. Moreover, the detector collects signals respectively corresponding to interactions between the sample and each of the electron patterns in the sequence. In this way, sequential global measurements can be made, rather than local, single-pixel measurements in conventional scanning electron microscopy.

According to various embodiments, the multi-beam generator can include a coded aperture that selectively allows portions of a source beam incident thereupon to pass through a subset of holes to the sample. For instance, the coded aperture can be a MEMS electrostatic array, a MEMS mechanical shutter array, a MEMS electromagnetic array, or a MEMS electrostatic mirror array. Additionally or alternatively, the multi-beam generator can include a MEMS array of multiple field emission sources in accordance with various embodiments. In some embodiments, the multi-beam generator can include a line source. In other embodiments, the multi-beam generator can include a laser and photo cathode surface.

Moreover, the compressive sensing electron microscope can include a pattern control component that can control the multi-beam generator to emit the sequence of the electron patterns over time. Further, the compressive sensing electron microscope can include a collection component that obtains measurement data from the signals received by the detector. The compressive sensing electron microscope can further include a reconstruction component that can employ a compressive sensing reconstruction algorithm to generate an image based on the measurement data.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
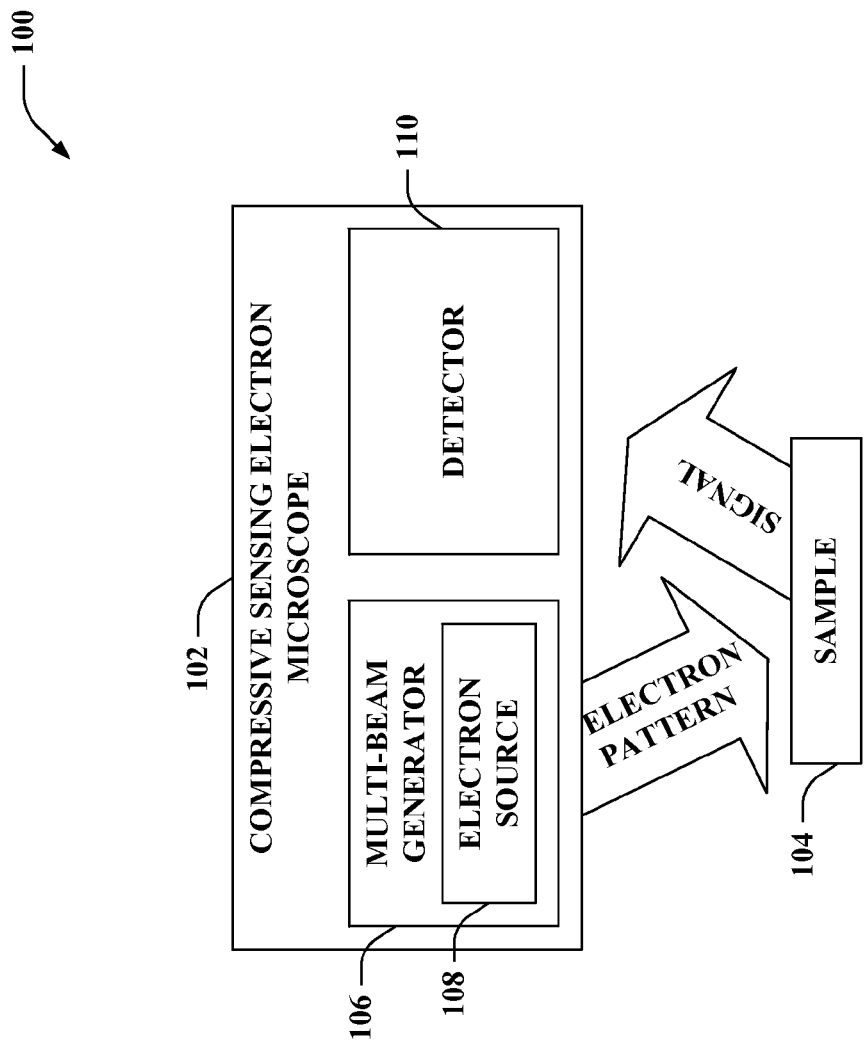
FIG. 1 illustrates a functional block diagram of an exemplary system that includes an exemplary compressive sensing electron microscope configured to image a sample.

Various technologies pertaining to electron microscopy that employs compressive sensing are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Referring now to the drawings, FIG. 1 illustrates a system 100 that includes an exemplary compressive sensing electron microscope 102 configured to image a sample 104. The compressive sensing electron microscope 102 includes a multi-beam generator 106 that emits a sequence of electron patterns over time. Each of the electron patterns in the sequence includes a plurality of electron beams. Moreover, the plurality of electron beams in each of the electron patterns is configured to impart a spatially varying electron density on the sample 104. The spatially varying electron density varies between each of the electron patterns in the sequence.

The multi-beam generator 106 further includes an electron source 108 that generates the electron beams. The electron source 108 can be substantially any type of source of electrons. According to an example, the electron source 108 can be an electron gun fitted with a tungsten filament cathode. By way of another example, the electron source 108 can be a lanthanum hexaboride ($LaB_6$) cathode. According to a further example, the electron source 108 can be a microelectromechanical systems (MEMS) array of field emitter sources. By way of another example, the electron source 108 can be a line source. Pursuant to yet another example, the electron source 108 can include a laser and a photo cathode surface; following this example, the laser can emit photons (e.g., project a pattern of light) that impinge on a first side of the photo cathode surface, and the photo cathode surface can emit electrons from a second side (e.g., opposite the first side) in response to the photons incident upon the first side. Yet, it is contemplated that the claimed subject matter is not limited to the foregoing examples.

Moreover, the compressive sensing electron microscope 102 includes a detector 110. The detector 110 collects signals respectively corresponding to interactions between sample 104 and each of the electron patterns in the sequence generated by the multi-beam generator 106. The detector 110, for example, can detect a response via substantially any mechanism (e.g., the detector 110 can detect secondary electrons, detect backscattered electrons, employ beam-injection analysis, etc.). According to an illustration, the multi-beam generator 106 can emit a first electron pattern during a first time period and can emit a second electron pattern during a second time period, where the first electron pattern and the second electron pattern can be incident upon the sample 104. The detector 110 can collect a first signal (e.g., a first response) corresponding to the interaction between the sample 104 and the first electron pattern. Moreover, the detector 110 can collect a second signal (e.g., a second response) corresponding to the interaction between the sample 104 and the second electron pattern.

By employing compressive sensing, a number of measurements obtained by the compressive sensing electron microscope 102 to generate an image can be a function of compressibility of a scene as opposed to Nyquist terms for a highest spatial frequency, which commonly underlies traditional scanning electron microscope techniques. Thus, with compressive sensing, useful information in an image can be acquired in fewer measurements as compared to conventional scanning electron microscopes. Compressive sensing techniques can employ compressive measurements and image reconstruction. The compressive measurements can be made using the sequence of electron patterns, which sample information in a field of view (e.g., at least a portion of the sample 104 upon which the electron patterns are incident). For instance, the electron patterns in the sequence can be complementary to a linear basis in which a traditional image is compressible. Moreover, a signal received by the detector 110 can be a weighted combination of interactions between a given electron pattern and pixels in the field of view. Further, as part of image reconstruction, compressive samples can be nonlinearly decompressed to form an image.

The compressive sensing electron microscope 102 includes a single detector, namely, the detector 110. Moreover, each response obtained using the detector 110 can include information spanning a desired image, thereby allowing fewer total measurements to be made when constructing an image of the sample 104. According to an example, a measurement obtained by the compressive sensing electron microscope 102 can be performed approximately as fast as a conventional scanning electron microscope measurement for an individual pixel; accordingly, total imaging time can be reduced significantly by employing the compressive sensing electron microscope 102 as compared to conventional scanning electron microscopes.

Moreover, the compressive sensing electron microscope 102 can decrease an amount of charge injected into the sample 104. For instance, as electrons are supplied to the surface of the sample 104, such electrons can affect the sample 104. Depending upon the makeup of the sample 104, the electrons may interact with the sample 104 (referred to as charging the sample 104), thereby resulting in different interactions being detected by the detector 110 via the received signals. Since the compressive sensing electron microscope 102 can inject fewer electrons on average to the sample 104 as compared to conventional approaches, effects of charging can be mitigated as compared to traditional scanning electron microscopy approaches. Some samples may also be contaminated by impinging electrons. The proposed approach would also reduce sample contamination in these cases.

Figure 3:
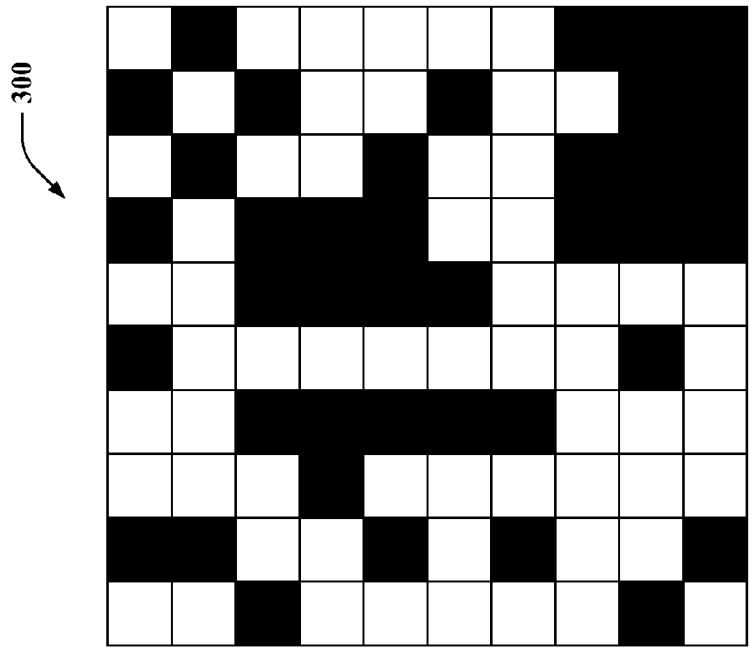
FIGS. 2-3 illustrate exemplary electron patterns that can be emitted by a multi-beam generator of the compressive sensing electron microscope of FIG. 1.
Figure 2:
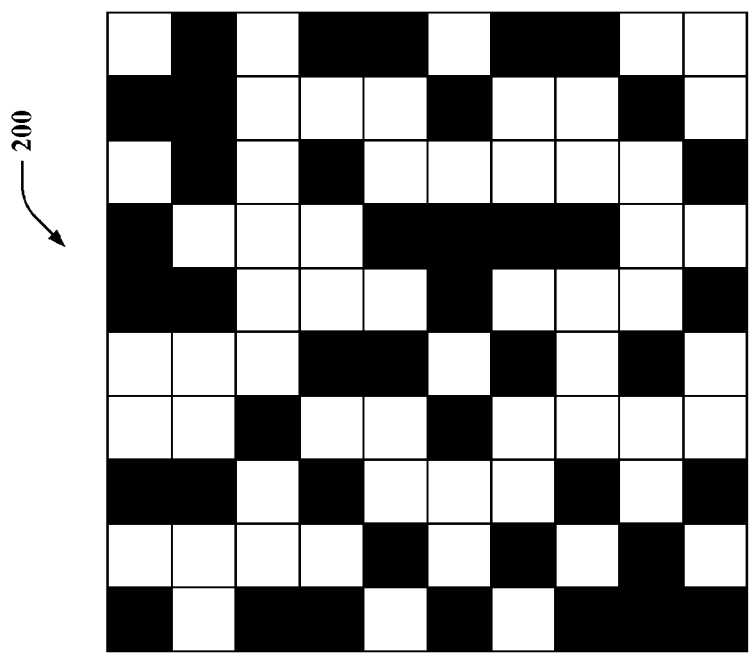

Now turning to FIGS. 2-3, illustrated are exemplary electron patterns that can be emitted by the multi-beam generator 106 of the compressive sensing electron microscope 102 of FIG. 1. The electron patterns are represented by pixel grids. According to an example, a pixel in a pixel grid can be on or off. If the pixel is on (e.g., represented by a black pixel in FIGS. 2-3), then an electron beam can be imparted onto the sample 104 at a location corresponding to such pixel. Moreover, if the pixel is off (e.g., represented by a white pixel in FIGS. 2-3), then an electron beam can be inhibited from being imparted onto the sample 104 at the location corresponding to such pixel.

More particularly, FIG. 2 illustrates a first electron pattern 200 and FIG. 3 illustrates a second electron pattern 300 (collectively referred to as electron patterns 200-300). The electron patterns 200-300 can be included within the sequence of electron patterns emitted by the multi-beam generator 106. Hence, as shown, the electron patterns in the sequence emitted by the multi-beam generator 106 differ over time.

Additionally, the electron patterns 200-300 are spatially varying. In particular, the electron pattern 200 includes a first subset of pixels that are on and a second subset of pixels that are off, and the electron pattern 300 includes a first subset of pixels that are on and a second subset of pixels that are off. The subsets of pixels that are on and the subsets of pixels that are off differ between the electron patterns 200-300.

While FIGS. 2-3 depict an exemplary illustration of electron patterns, it is contemplated that claimed subject matter is not so limited. For instance, pixels grids that include substantially any number of pixels are intended to fall within the scope of the hereto appended claims. Moreover, various beam shapes are intended to fall within the scope of the hereto appended claims. Further, the claimed subject matter is not limited to a pixel being on or off (e.g., a number of gray levels can be used for pixels). In accordance with yet other embodiments, pixel grids need not be employed (e.g., an electron pattern can be spatially varying without pixelization).

Figure 4:
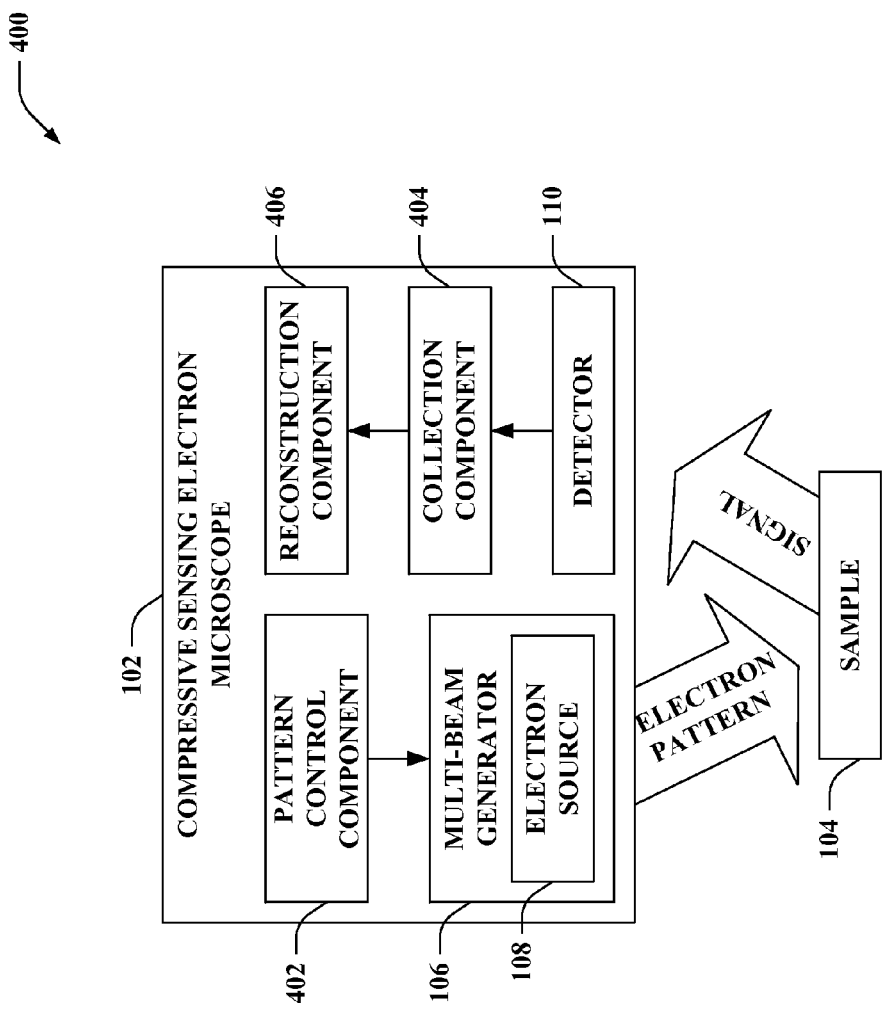
FIG. 4 illustrates a functional block diagram of another exemplary system that performs compressive sensing electron microscopy.

With reference to FIG. 4, illustrated is another exemplary system 400 that performs compressive sensing electron microscopy. The system 400 includes the compressive sensing electron microscope 102, which images the sample 104. Similar to above, the compressive sensing electron microscope 102 includes the multi-beam generator 106, which can further include the electron source 108. The multi-beam generator 106 emits a sequence of electron patterns over time. Moreover, the compressive sensing electron microscope 102 includes the detector 110, which collects signals respectively corresponding to interactions between the sample 104 and each of the electron patterns in the sequence generated by the multi-beam generator 106.

The compressive sensing electron microscope 102 further includes a pattern control component 402 that controls the multi-beam generator 106 to emit the sequence of the electron patterns over time. Further, the compressive sensing electron microscope 102 includes a collection component 404 that obtains measurement data from the signals respectively corresponding to the interactions between the sample 104 and each of the electron patterns in the sequence as received by the detector 110. The compressive sensing electron microscope 102 also includes a reconstruction component 406 that employs a compressive sensing reconstruction algorithm to generate an image of the sample 104 based on the measurement data obtained by the collection component 404. It is contemplated that the reconstruction component 406 can employ substantially any compressive sensing reconstruction algorithm. Further, it is contemplated that the image generated by the reconstruction component 406 can be rendered on a display screen, retained in a data repository, or the like.

The pattern control component 402 can employ various algorithms to control the multi-beam generator 106. According to an example, the pattern control component 402 can employ a model-based algorithm to control the multi-beam generator 106 to emit the sequence of the electron patterns over time. Following this example, the electron patterns in the sequence can be selected by the pattern control component 402 based upon a property of the sample 104. By having knowledge of the property of the sample prior to imaging, the process of generating the image from the electron patterns can be more efficient; hence, the model-based algorithm can be implemented to decrease a number of electron patterns generated by the multi-beam generator 106 and a corresponding number of signals collected by the detector 110 when reconstructing an image of the sample 104.

According to another example, the pattern control component 402 can employ an adaptive algorithm to control the multi-beam generator 106 to emit the sequence of the electron patterns over time. Pursuant to such example, the electron patterns in the sequence can be selected by the pattern control component 402 based upon previously obtained measurement data. Accordingly, feedback from the collection component 404 and/or the reconstruction component 406 can be utilized by the pattern control component 402 when controlling the multi-beam generator 106 in connection with emitting the sequence of the electron patterns over time. By employing an adaptive algorithm, the pattern control component 402 can control generation of a given electron pattern based upon data previously collected by the detector 110, the Collection component 404, and/or the reconstruction component 406, reducing the number patterns generated to reconstruct an image.

The pattern control component 402 can select electron patterns that are complementary to a linear basis in which an image is compressible. For instance, the electron patterns may be compatible with the Haar compression basis, the total-variation basis, or a domain-specific, overcomplete dictionary. Yet, the claimed subject matter is not so limited.

The multi-beam generator 106 can impart a tunable spatial electron density, for example, via electrostatic meshes, electromagnetic deflection, spatial sources, MEMS shutters, and the like. Yet, it is contemplated that substantially any manner of supplying multiple beams by the multi-beam generator 106 is intended to fall within the scope of the hereto appended claims. Moreover, the pattern control component 402 can control such generation by the multi-beam generator 106.

With reference to FIGS. 5-8, illustrated are various exemplary electron patterns that can be employed in connection with the claimed subject matter. It is contemplated, however, that the claimed subject matter is not limited to the following example electron patterns. The electron patterns are each shown upon a pixel grid. Again, it is contemplated that substantially any number of pixels can be included in a pixel grid (e.g., the pixel grid can be 1000 by 1000, etc.), and the claimed subject matter is not limited to the illustrated example.

Figure 6:
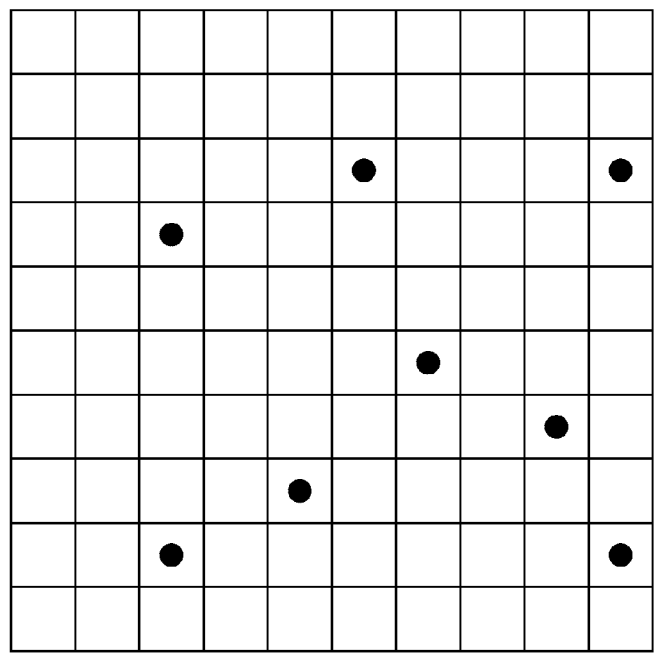
FIGS. 5-8 illustrate various exemplary electron patterns that can be employed in connection with the claimed subject matter.
Figure 5:
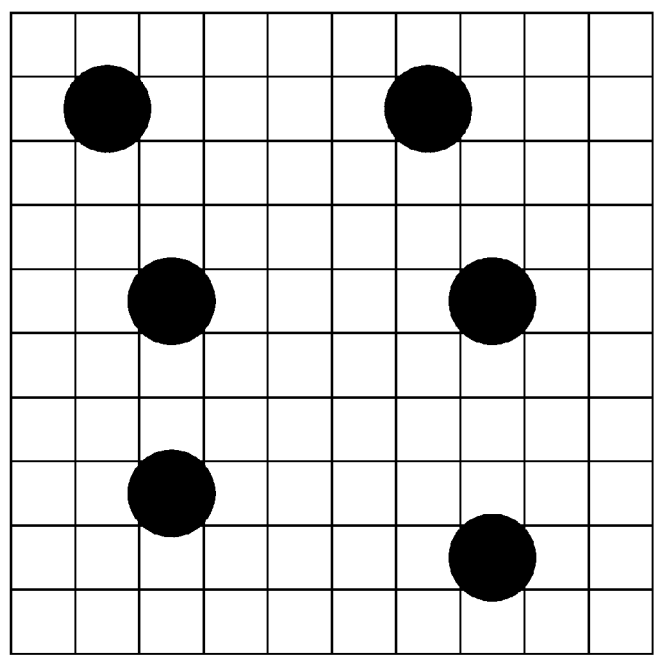
Figure 7:
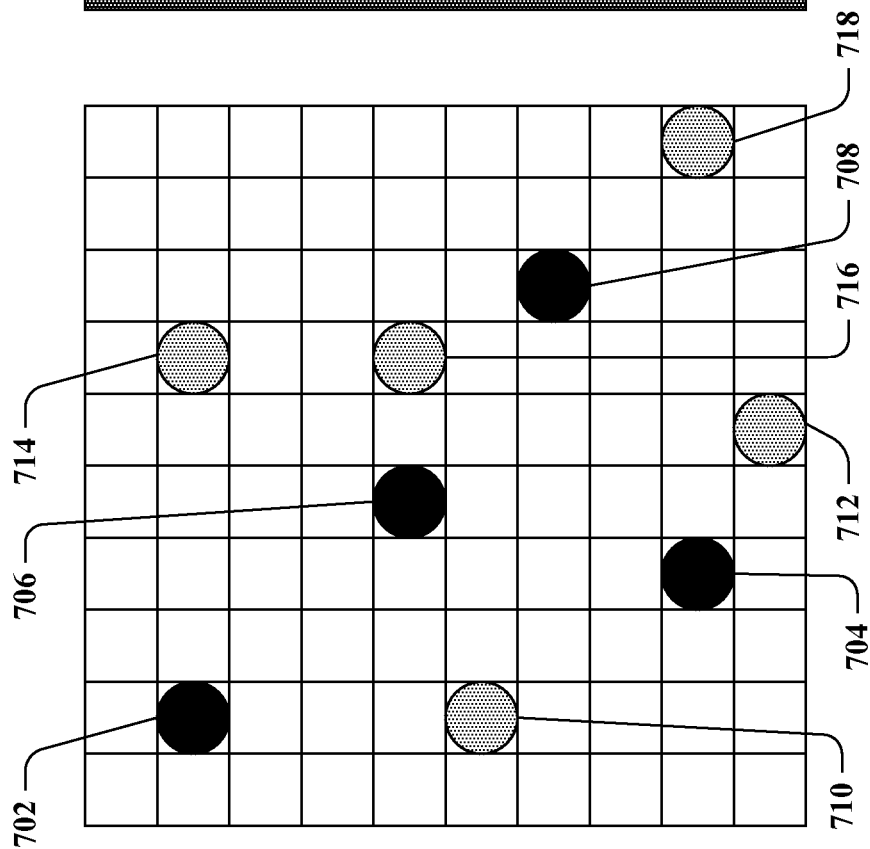

According to an example, the plurality of electron beams in each of the electron patterns generated by the multi-beam generator 106 can be a plurality of Gaussian shaped beams having respective beam spots centered on corresponding pixels in a pixel grid. Thus, a subset of the pixels in the pixel grid can lack beam spots centered thereupon. More particularly FIGS. 5-7 illustrate examples of such Gaussian shaped beams being utilized within the electron patterns generated by the multi-beam generator 106. While the beam spots are described as being centered on corresponding pixels, it is also contemplated that beam spots can be positioned off-axis with respect to the corresponding pixels, etc.

FIG. 5 illustrates an electron pattern that includes Gaussian shaped beams having respective beam spots that are greater than a pixel spacing in the pixel grid. As shown, the Gaussian shaped beam spots are centered on respective pixels within the pixel grid. Moreover, the beam spots have sizes that are greater than the pixel spacing within the pixel grid.

Turning to FIG. 6, illustrated is an electron pattern that includes a plurality of Gaussian shaped beams having respective beam spots that have sizes that are less than a pixel spacing in the pixel grid. Again, the beam spots are centered on respective pixels within the pixel grid. As depicted, sizes of the beam spots in FIG. 6 are less than the pixel spacing within the pixel grid.

Referring now to FIG. 7, illustrated is an electron pattern that includes a plurality of Gaussian shaped beams. As illustrated in FIG. 7, a first set of the plurality of Gaussian shaped beams can have a first electron density; for instance, the Gaussian shaped beams 702-708 can have a first electron density. Moreover, a second subset of the plurality of the Gaussian shaped beams can have a second electron density; namely, the Gaussian beams 710-718 can have a second electron density. Further, the first electron density differs from the second electron density. By employing differing electron densities, pixels can be illuminated with some number of gray levels. It is contemplated that substantially any number of differing electron densities can be utilized within the electron pattern, and the claimed subject matter is not limited to use of two such electron densities as illustrated in FIG. 7.

Figure 8:
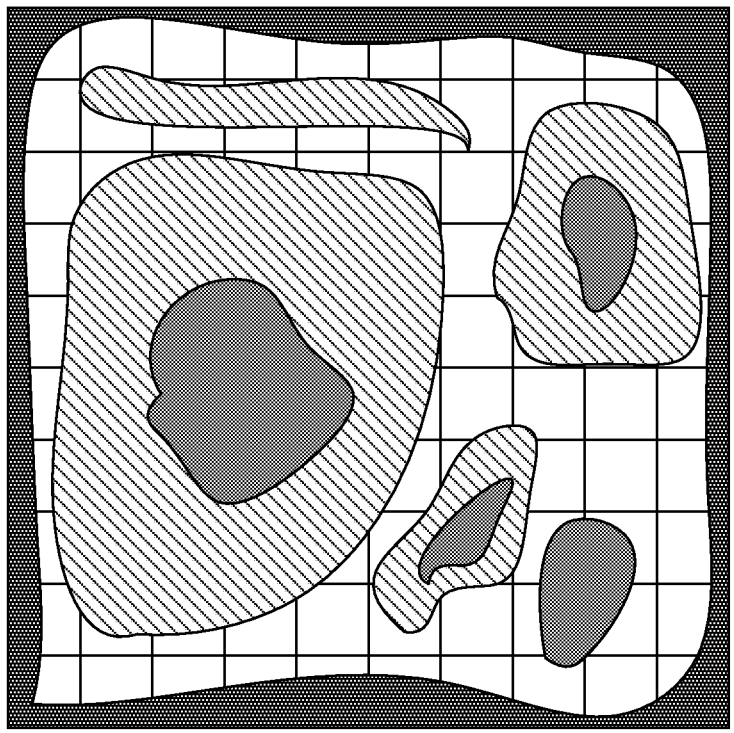

Now referring to FIG. 8, illustrated is an electron pattern which includes spatially varying electron density imparted on a sample that lacks pixelization. In accordance with this example, the electron density imparted on the sample 104 by the multi-beam generator 106 can be controlled in a gradational manner. Accordingly, a grayscale pattern that lacks pixels can be imparted upon the sample 104.

While various electron patterns are illustrated herein, it is to be appreciated that substantially any other type of electron pattern that is spatially varying is intended to fall within the scope of the hereto appended claims.

Various exemplary embodiments of the multi-beam generator 106 of the compressive sensing electron microscope 102 are set forth below. It is contemplated that the embodiments of the multi-beam generator 106 provided below can further include extractors, accelerators, lenses, and so forth.

Figure 9:
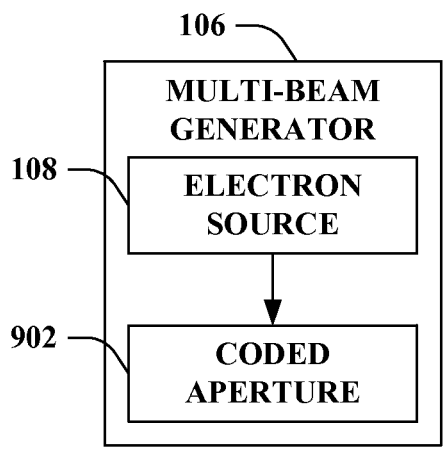
FIG. 9 illustrates a functional block diagram of an exemplary embodiment of the multi-beam generator of FIG. 1.

Now turning to FIG. 9, illustrated is the multi-beam generator 106 in accordance with various embodiments. The multi-beam generator 106 as shown in FIG. 9 includes the electron source 108 that creates an electric field. For instance; the electron source 108 can be at a top of a column of the compressive sensing electron microscope 102. Moreover, electrons from the electron field generated by the electron source 108 can be drawn away from the electron source 108 and sent down the column in a source beam.

The multi-beam generator 106 further includes a coded aperture 902 that includes a set of holes. The coded aperture 902 can selectively allow portions of the source beam to pass through a first subset of the holes and can inhibit disparate portions of the source beam from passing through a second subset of the holes over time to form the plurality of electron beams in each of the electron patterns generated by the multi-beam generator 106. For example, a given hole in the set can either allow a corresponding portion of the source beam to pass there through or inhibit the corresponding portion of the source beam to pass there through during a given time period. Following this example, whether the given hole allows or inhibits passage of the corresponding portion of the source beam can be altered during a disparate time period.

Moreover, the coded aperture 902 can be selectively controlled by the pattern control component 402 of FIG. 4. Accordingly, the pattern control component 402 can selectively control the first subset of the holes to allow portions of the source beam incident upon the coded aperture 902 to pass there through and can control the second subset of the holes to inhibit disparate portions of the source beam incident upon the coded aperture 902 from passing there through over time, thereby forming the plurality of electron beams in each of the electron patterns generated by the multi-beam generator 106.

Various types of coded apertures are intended to fall within the scope of the hereto appended claims. For instance, the coded aperture 902 can be a MEMS electrostatic array. A MEMS electrostatic array can be an electrostatic mesh that can control whether portions of the source beam pass through the coded aperture 902 and/or are inhibited by the coded aperture 902. By way of another example, the coded aperture 902 can be a MEMS mechanical shutter array. A MEMS mechanical shutter array can include MEMS shutters that can mechanically open and close to selectively permit portions of the source beam to pass through the holes or inhibit such portions of the source beam from passing through the holes during given time periods. Pursuant to yet another example, the coded aperture 902 can be a MEMS electromagnetic array. A MEMS electromagnetic array can provide electromagnetic deflection of portions of the source beam. By way of another example, the coded aperture 902 can be a MEMS electrostatic mirror array; such MEMS electrostatic mirror array can include electrostatic deflection mirrors that direct some of the impinging beams toward the sample and other impinging beams away. It is contemplated, however, that the claimed subject matter is not limited to the foregoing examples.

It is contemplated that substantially any type of design of the coded aperture 902 is intended to fall within the scope of the hereto appended claims. According to an example, the coded aperture 902 can include an aperture plate and a blanking plate. The aperture plate can include a plurality of holes and the blanking plate can selectively allow portions of the source beam passing through such holes to continue to a sample or to be inhibited. Yet, it is contemplated that the claimed subject matter is not so limited.

Figure 10:
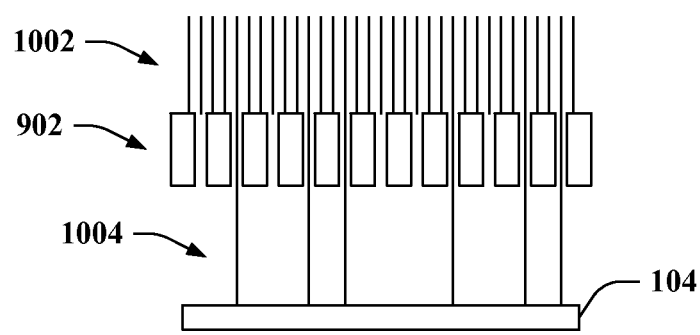
FIG. 10 illustrates an exemplary schematic view of the coded aperture of the multi-beam generator of FIG. 9.

Now turning to FIG. 10, illustrated is an exemplary schematic view of the coded aperture 902. The coded aperture 902 includes a plurality of holes that pass there through. A source beam 1002 is incident upon the coded aperture 902. Portions of the source beam 1002 can pass through a subset of the holes included in the coded aperture 902, while disparate holes included in the coded aperture 902 can inhibit portions of the source beam 1002 from passing there through. As noted above, the coded aperture 902 can include various mechanisms to selectively permit or inhibit portions of the source beam 1002 from passing through each of the holes. Portions of the source beam 1002 that pass through the subset of the holes included in the coded aperture 902 can be the plurality of electron beams 1004 included in an electron pattern. Further, the plurality of electron beams 1004 can be imparted upon the sample 104. It is to be appreciated, however, that the claimed subject matter is not limited to the example set forth in FIG. 10.

Figure 11:
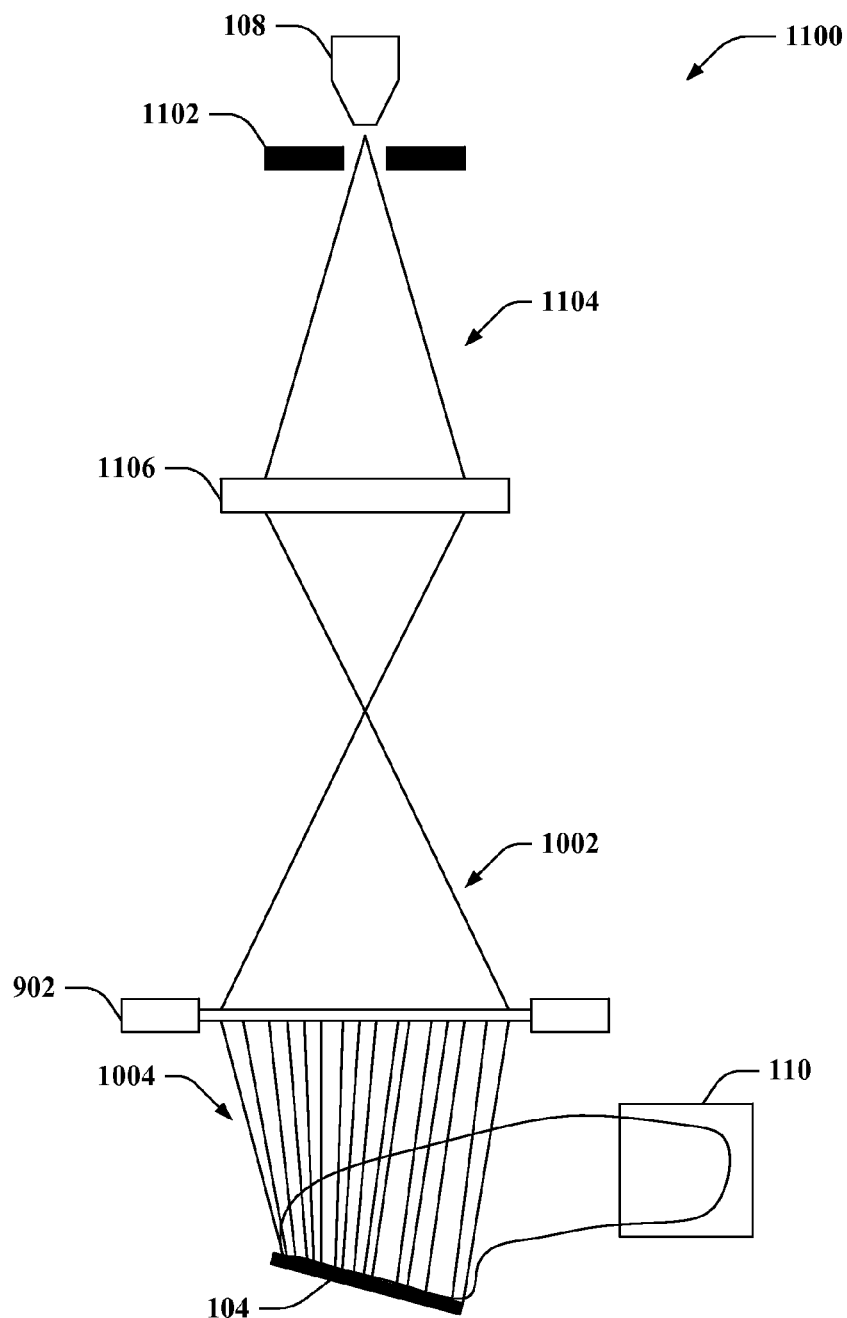
FIG. 11 illustrates an exemplary schematic view of an exemplary compressive sensing electron microscope.

Now turning to FIG. 11, illustrated is a compressive sensing electron microscope 1100. The compressive sensing electron microscope 1100 includes the electron source 108, which creates an electron field. Moreover, although not shown, the compressive sensing electron microscope 1100 can include an extractor that can pull electrons from the electric field generated around the electron source 108. The compressive sensing electron microscope 1100 further includes an accelerator 1102 that drives the electrons pulled from the electron field by the extractor away from the electron source 108 and sends such electrons down the column of the compressive sensing electron microscope 1100. The electrons can be sent down the column of the compressive sensing electron microscope 1100 in a source beam 1104. The source beam 1104 can pass through a condenser lens 1106 to provide the source beam 1002.

The source beam 1002 can be incident upon the coded aperture 902, which can selectively allow portions of the source beam 1002 to pass through a first subset of the holes of the coded aperture 902 while inhibiting disparate portions of the source beam 1002 from passing through a second subset of the holes over time to form the electron beams 1004 in each of the electron patterns, which can be imparted on the sample 104. Accordingly, the coded aperture 902 can be a mechanism whereby parts of a broad beam of electrons can selectively be allowed to proceed to the sample 104, while other parts of the broad beam of electrons are inhibited from proceeding to the sample 104. Moreover, the detector 110 can receive a signal indicative of interactions between the sample 104 and each of the electron patterns in the sequence. Thus, interaction of the electron beams 1004 with the sample 104 can be obtained by the detector 110.

By employing an electron pattern at a given time, where such electron pattern can be imparted upon the sample 104, a single measurement can be made by the detector 110 for an entire field of interest. Such single measurement at a given time can be made by selectively switching which part of the field of interest to supply with electron beams for such single measurement. In comparison to a conventional scanning electron microscopy technique that individually measures each pixel (e.g., 1,000,000 individual measurements can be made for a 1000 by 1000 field of view), use of the compressive sensing electron microscope 1100 can significantly reduce the number of measurements by collecting different types of information about the entire field of view in a series of measurements (e.g., compressive measurements) rather than taking individual measurements for each of the pixels in the field of view.

Figure 12:
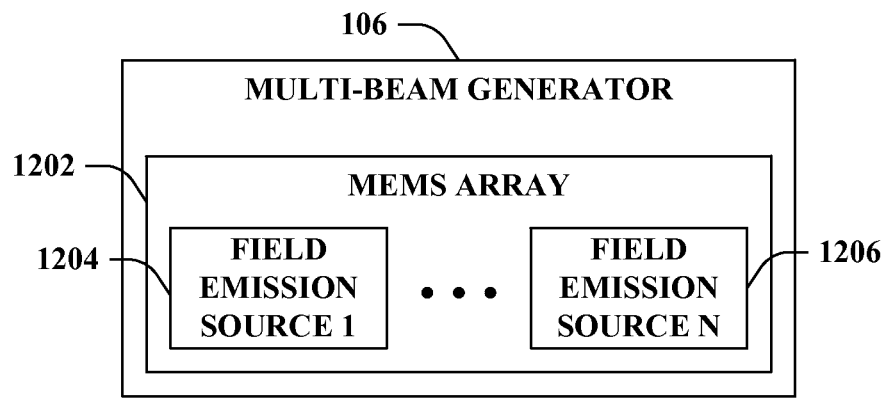
FIGS. 12-15 illustrate functional block diagrams of other exemplary embodiments of the multi-beam generator of FIG. 1.

Turning to FIG. 12, illustrated is another exemplary embodiment of the multi-beam generator 106. As shown in FIG. 12, the multi-beam generator 106 includes a MEMS array 1202. The MEMS array 1202 includes a plurality of field emission sources, namely, a field emission source 1 1204, . . . , and a field emission source N 1206 (collectively referred to herein as field emission sources 1204-1206), where N can be substantially any integer greater than two. The field emission sources 1204-1206 of the MEMS array 1202, for example, can be integrated gate electrodes with dielectric separation to allow high voltages and mitigate tip breakdown.

The field emission sources 1204-1206 are each selectively controllable. Moreover, a first subset of the field emission sources 1204-1206 are enabled to create respective electron fields from which electrons are drawn and sent down a column of the compressive sensing electron microscope 102 in corresponding source beams. Further, a second subset of the field emission sources 1204-1206 are disabled. The first subset and the second subset can vary over time. Moreover, the plurality of electron beams in each of the electron patterns can be formed from the source beams. According to an example, the pattern control component 402 of FIG. 4 can selectively control each of the field emission sources 1204-1206 of the MEMS array 1202. The pattern control component 402 can control, over time, the first subset of the field emission sources 1204-1206 that are enabled, and the second subset of the field emission sources 1204-1206 that are disabled.

Each of the field emission sources 1204-1206 can be individually addressable; hence, the field emission sources 1204-1206 can be separately controllable. Moreover, it is contemplated that respective apertures can be utilized for each of the field emission sources 1204-1206 to divide beams emitted therefrom into separate beamlets. However, it is contemplated that the claimed subject matter is not so limited.

Figure 13:
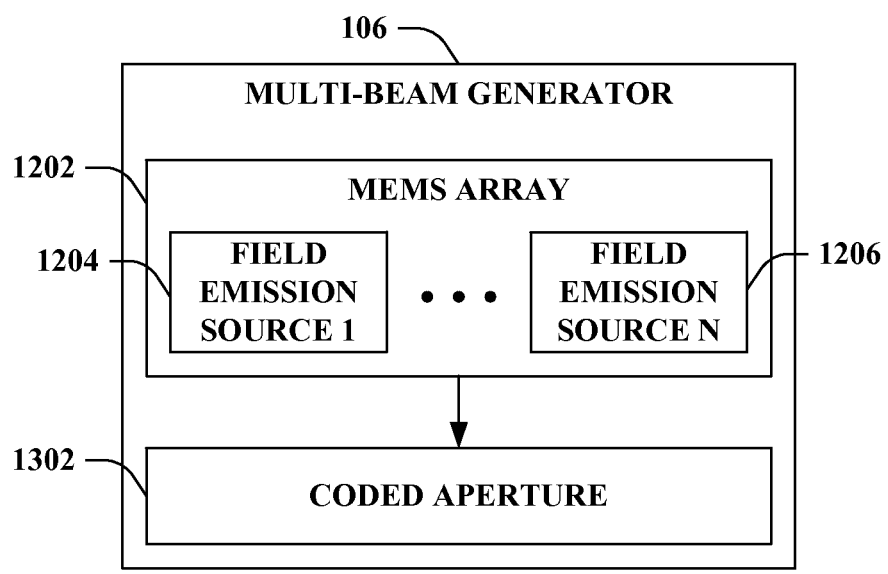

Turning to FIG. 13, illustrated is another exemplary embodiment of the multi-beam generator 106. The multi-beam generator 106 of FIG. 13 includes the MEMS array 1202, which further includes the field emission sources 1204-1206. Moreover, the multi-beam generator 106 includes a coded aperture 1302 that includes a set of holes (e.g., the coded aperture 1302 can be substantially similar to the coded aperture 902 of FIG. 9). The coded aperture 1302 can selectively allow portions of the source beam generated by each of the field emission sources 1204-1206 to pass through a first subset of the holes. Moreover, the coded aperture 1302 can inhibit disparate portions of the source beam from each of the field emission sources 1204-1206 from passing through a second subset of the holes. The foregoing can be performed over time to form the plurality of the electron beams in each of the electron patterns generated by the multi-beam generator 106.

Again, it is to be appreciated that the MEMS array 1202 and the coded aperture 1302 can be controlled by the pattern control component 402 of FIG. 4; yet, the claimed subject matter is not so limited.

Figure 14:
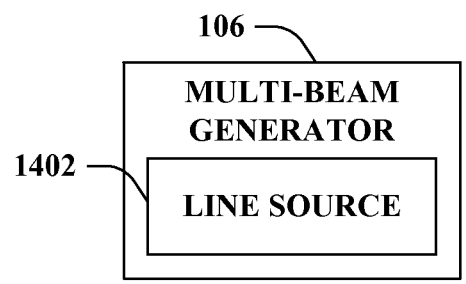

Now turning to FIG. 14, illustrated is yet another exemplary embodiment of the multi-beam generator 106. The multi-beam generator 106 in FIG. 14 includes a line source 1402 that supplies electrons in the plurality of the electron beams in each of the electron patterns generated by the multi-beam generator 106. Accordingly, the line source 1402 can be the electron source 108 of FIG. 1.

Figure 15:
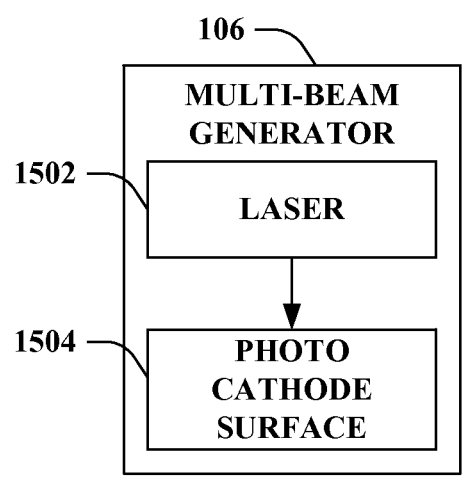

Referring now to FIG. 15, illustrated is another exemplary embodiment of the multi-beam generator 106. As depicted in FIG. 15, the multi-beam generator 106 includes a laser 1502 and a photo cathode surface 1504. The laser 1502 can project a pattern of light onto a first side of the photo cathode surface 1504. Moreover, the photo cathode surface 1504 can convert the pattern of light projected by the laser 1502 incident upon the first side thereof into electrons, whereby the electrons can be emitted from a second side of the photo cathode surface 1504. The electrons emitted from the second side of the photo cathode surface 1504 can form the sequence of electron patterns over time. Further, it is contemplated that a set of lasers can be configured to create the electron patterns by projecting the pattern of light onto the photo cathode surface 1504, where a like pattern of electrons is generated on the other side of the photo cathode surface 1504, which can travel down a column of the compressive sensing electron microscope.

Figure 16:
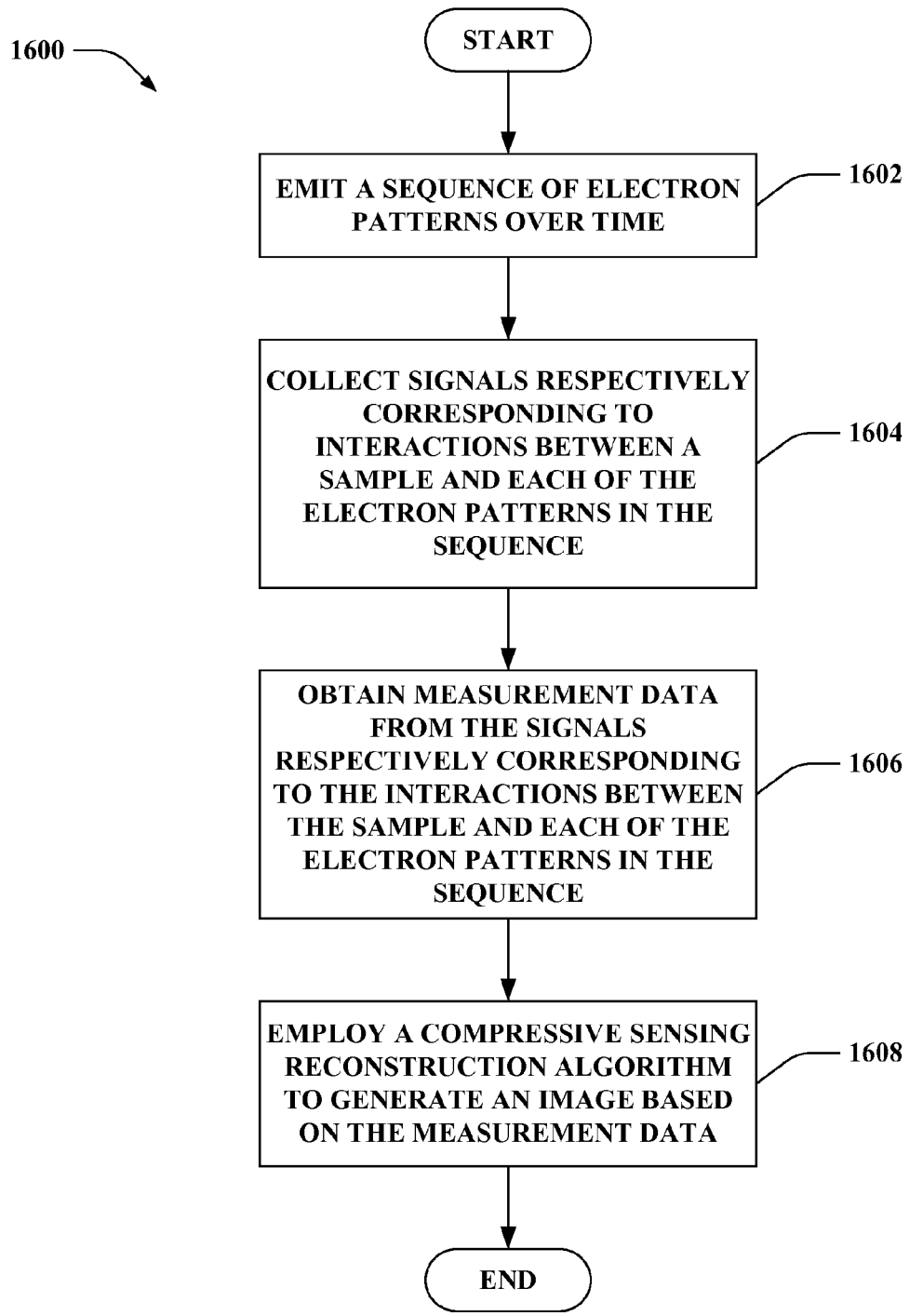
FIG. 16 is a flow diagram that illustrates an exemplary methodology of employing a compressive sensing electron microscope to generate an image of a sample.

FIG. 16 illustrates exemplary methodologies relating to utilizing compressive sensing electron microscopy. While the methodology is shown and described as being a series of acts that are performed in a sequence, it is to be understood and appreciated that the methodology is not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

FIG. 16 illustrates a methodology 1600 of employing a compressive sensing electron microscope to generate an image of a sample. At 1602, a sequence of electron patterns can be emitted over time. Each of the electron patterns in the sequence can include a plurality of electron beams. Moreover, the plurality of the electron beams in each of the electron patterns can be configured to impart a spatially varying electron density on the sample. Further, the spatially varying electron density can vary between each of the electron patterns in the sequence.

At 1604, signals respectively corresponding to interactions between the sample and each of the electron patterns in the sequence can be collected. At 1606, measurement data from the signals respectively corresponding to the interactions between the sample and each of the electron patterns in the sequence can be obtained. At 1608, a compressive sensing reconstruction algorithm can be employed to generate an image based on the measurement data.

Figure 17:
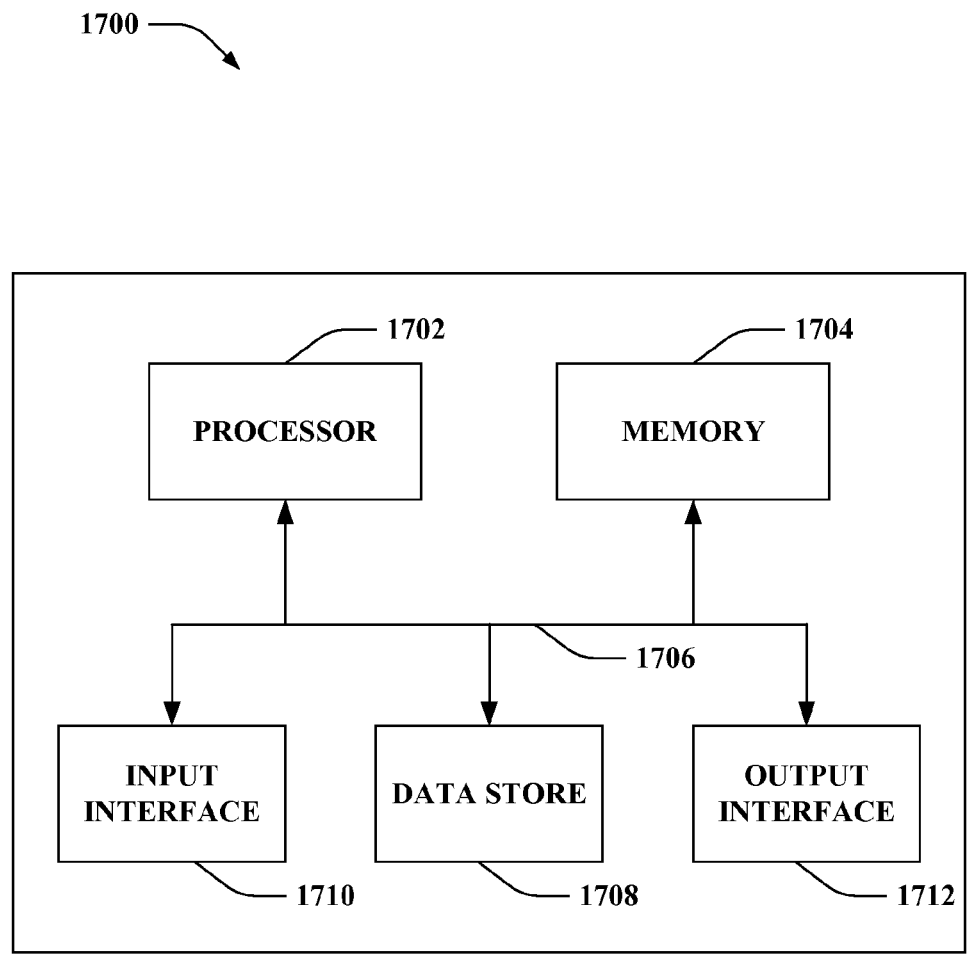
FIG. 17 illustrates an exemplary computing device.

Referring now to FIG. 17, a high-level illustration of an exemplary computing device 1700 that can be used in accordance with the systems and methodologies disclosed herein is illustrated. For instance, the computing device 1700 may be used in a system that employs compressive sensing electron microscopy. According to an example, the computing device 1700 can control a multi-beam generator to emit a sequence of electron patterns over time. Further, the computing device 1700 can obtain measurement data from signals received by a detector. Moreover, the computing device 1700 can employ a compressive sensing reconstruction algorithm to generate an image based on the measurement data. The computing device 1700 can further cause the image to be rendered upon a display screen, retained in a data repository, or the like. The computing device 1700 includes at least one processor 1702 that executes instructions that are stored in a memory 1704. The instructions may be, for instance, instructions for implementing functionality described as being carried out by one or more components discussed above or instructions for implementing one or more of the methods described above. The processor 1702 may access the memory 1704 by way of a system bus 1706. In addition to storing executable instructions, the memory 1704 may also store an image, measurement data, information related to a property of a sample, and so forth.

The computing device 1700 additionally includes a data store 1708 that is accessible by the processor 1702 by way of the system bus 1706. The data store 1708 may include executable instructions, an image, measurement data, information related to a property of a sample, etc. The computing device 1700 also includes an input interface 1710 that allows external devices to communicate with the computing device 1700. For instance, the input interface 1710 may be used to receive instructions from an external computer device, from a user, etc. The computing device 1700 also includes an output interface 1712 that interfaces the computing device 1700 with one or more external devices. For example, the computing device 1700 may display text, images, etc. by way of the output interface 1712.

Additionally, while illustrated as a single system, it is to be understood that the computing device 1700 may be a distributed system. Thus, for instance, several devices may be in communication by way of a network connection and may collectively perform tasks described as being performed by the computing device 1700.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

Further, as used herein, the term "exemplary" is intended to mean "serving as an illustration or example of something."

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A compressive sensing electron microscope comprising:
a multi-beam generator that emits a sequence of electron patterns over time, wherein each of the electron patterns in the sequence comprises a plurality of electron beams, wherein the plurality of the electron beams in each of the electron patterns is configured to impart a spatially varying electron density on a sample, wherein the spatially varying electron density varies between each of the electron patterns in the sequence, and wherein each of the electron patterns is complementary to a linear basis in which a traditional image of the sample is compressible;
a detector that collects signals respectively corresponding to interactions between the sample and each of the electron patterns in the sequence;
a collection component that obtains measurement data from the signals respectively corresponding to the interactions between the sample and each of the electron patterns in the sequence; and
a reconstruction component that employs a compressive sensing reconstruction algorithm to generate an image based on the measurement data.

2. The compressive sensing electron microscope of claim 1, wherein the plurality of the electron beams in each of the electron patterns are a plurality of Gaussian shaped beams having respective beam spots centered on corresponding pixels in a pixel grid, and wherein a subset of pixels in the pixel grid lack beam spots centered thereupon.

3. The compressive sensing electron microscope of claim 2, wherein a size of the beam spots is greater than a pixel spacing in the pixel grid.

4. The compressive sensing electron microscope of claim 2, wherein a size of the beam spots is less than a pixel spacing in the pixel grid.

5. The compressive sensing electron microscope of claim 2, wherein a first subset of the plurality of the Gaussian shaped beams have a first electron density, and a second subset of the plurality of the Gaussian shaped beams have a second electron density, wherein the first electron density differs from the second electron density.

6. The compressive sensing electron microscope of claim 1, wherein the spatially varying electron density imparted on the sample lacks pixelization.

7. The compressive sensing electron microscope of claim 1, wherein the multi-beam generator comprises:
an electron source that creates an electron field, wherein the electron source is at a top of a column of the compressive sensing electron microscope, and wherein electrons from the electron field are drawn away from the electron source and sent down the column in a source beam; and
a coded aperture that comprises a set of holes, wherein the coded aperture selectively allows portions of the source beam to pass through a first subset of the holes and inhibits disparate portions of the source beam from passing through a second subset of the holes over time to form the plurality of the electron beams in each of the electron patterns.

8. The compressive sensing electron microscope of claim 7, wherein the coded aperture is at least one of a MEMS electrostatic array, a MEMS mechanical shutter array, a MEMS electromagnetic array, or a MEMS electrostatic mirror array.

9. The compressive sensing electron microscope of claim 1, wherein the multi-beam generator comprises a MEMS array of multiple field emission sources, wherein the field emission sources are each selectively controllable, wherein a first subset of the field emission sources are enabled to create respective electron fields from which electrons are drawn and sent down a column of the compressive sensing electron microscope in corresponding source beams and a second subset of the field emission sources are disabled over time, and wherein the plurality of the electron beams in each of the electron patterns are formed from the source beams.

10. The compressive sensing electron microscope of claim 9, wherein the multi-beam generator further comprises a coded aperture that comprises a set of holes, wherein the coded aperture selectively allows portions of the source beams to pass through a first subset of the holes and inhibits disparate portions of the source beams from passing through a second subset of the holes over time to form the plurality of the electron beams in each of the electron patterns.

11. The compressive sensing electron microscope of claim 1, wherein the multi-beam generator comprises a line source that supplies electrons in the plurality of the electron beams in each of the electron patterns.

12. The compressive sensing electron microscope of claim 1, wherein the multi-beam generator comprises:
a laser; and
a photo cathode surface;
wherein the laser projects a pattern of light onto a first side of the photo cathode surface, and wherein the photo cathode surface converts the pattern of light into electrons emitted from a second side of the photo cathode surface to form the sequence of electron patterns over time.

13. The compressive sensing electron microscope of claim 1, further comprising a pattern control component that controls the multi-beam generator to emit the sequence of the electron patterns over time.

14. A compressive sensing electron microscope comprising:
a multi-beam generator that emits a sequence of electron patterns over time, wherein each of the electron patterns in the sequence comprises a plurality of electron beams, wherein the plurality of the electron beams in each of the electron patterns is configured to impart a spatially varying electron density on a sample, and wherein the spatially varying electron density varies between each of the electron patterns in the sequence;
a pattern control component that controls the multi-beam generator to emit the sequence of the electron patterns over time;
a detector that collects signals respectively corresponding to interactions between the sample and each of the electron patterns in the sequence;
a collection component that obtains measurement data from the signals respectively corresponding to the interactions between the sample and each of the electron patterns in the sequence; and
a reconstruction component that employs a compressive sensing reconstruction algorithm to generate an image based on the measurement data.

15. The compressive sensing electron microscope of claim 14, wherein the pattern control component employs a model-based algorithm to control the multi-beam generator to emit the sequence of the electron patterns over time, wherein the electron patterns in the sequence are selected by the pattern control component based upon a property of the sample.

16. The compressive sensing electron microscope of claim 14, wherein the pattern control component employs an adaptive algorithm to control the multi-beam generator to emit the sequence of the electron patterns over time, wherein the electron patterns in the sequence are selected by the pattern control component based upon previously obtained measurement data.

17. The compressive sensing electron microscope of claim 14, wherein the multi-beam generator comprises a coded aperture that comprises a set of holes, and wherein the pattern control component selectively controls a first subset of the holes to allow portions of a source beam incident upon the coded aperture to pass there through and controls a second subset of the holes to inhibit disparate portions of the source beam incident upon the coded aperture from passing there through to form the plurality of the electron beams in each of the electron patterns.

18. The compressive sensing electron microscope of claim 14, wherein the multi-beam generator comprises a MEMS array of multiple field emission sources, wherein the pattern control component selectively controls each of the field emission sources, wherein a first subset of the field emission sources are enabled by the pattern control component to create respective electron fields from which electrons are drawn and sent down a column of the compressive sensing electron microscope in corresponding source beams and a second subset of the field emission sources are disabled by the pattern control component over time, and wherein the plurality of the electron beams in each of the electron patterns are formed from the source beams.

19. A method of employing a compressive sensing electron microscope to generate an image of a sample, the method comprising:
  emitting a sequence of electron patterns over time, wherein each of the electron patterns in the sequence comprises a plurality of electron beams, wherein the plurality of the electron beams in each of the electron patterns is configured to impart a spatially varying electron density on the sample, and wherein the spatially varying electron density varies between each of the electron patterns in the sequence;
  collecting signals respectively corresponding to interactions between the sample and each of the electron patterns in the sequence;
  obtaining measurement data from the signals respectively corresponding to the interactions between the sample and each of the electron patterns in the sequence; and
  employing a compressive sensing reconstruction algorithm to generate an image based on the measurement data.

* * * * *